(12) United States Patent
Smith

(10) Patent No.: US 6,575,898 B2
(45) Date of Patent: Jun. 10, 2003

(54) METHODS AND DEVICES FOR EX VIVO IRRADIATION OF AUTOLOGOUS CORONARY BYPASS CONDUIT

(75) Inventor: Robin G. Smith, Estill Springs, TN (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 10/040,599

(22) Filed: Nov. 1, 2001

(65) Prior Publication Data

US 2002/0128534 A1 Sep. 12, 2002

Related U.S. Application Data

(63) Continuation of application No. 08/999,290, filed on Dec. 29, 1997, now Pat. No. 6,419,625.
(60) Provisional application No. 60/035,739, filed on Jan. 3, 1997, and provisional application No. 60/040,293, filed on Feb. 11, 1997.

(51) Int. Cl.⁷ .............................................. A61B 19/00
(52) U.S. Cl. ............................................. 600/36; 600/1
(58) Field of Search ................................ 128/897, 898; 600/1–8, 36

(56) References Cited

U.S. PATENT DOCUMENTS

| | | |
|---|---|---|
| 3,916,874 A | 11/1975 | Perrin |
| 3,974,526 A | 8/1976 | Dardik et al. |
| 4,233,517 A | 11/1980 | Van't Hooft |
| 4,584,991 A | 4/1986 | Tokita et al. |
| 4,586,490 A | 5/1986 | Katz |
| 4,690,684 A | 9/1987 | McGreevy et al. |
| 5,059,166 A | 10/1991 | Fischell et al. |
| 5,092,841 A | 3/1992 | Spears |
| 5,100,425 A | 3/1992 | Fischell et al. |
| 5,103,395 A | 4/1992 | Spako et al. |
| 5,104,404 A | 4/1992 | Wolff |
| 5,108,417 A | 4/1992 | Sawyer |
| 5,110,429 A | 5/1992 | Novotny et al. |
| 5,110,810 A | 5/1992 | Eich et al. |
| 5,139,473 A | 8/1992 | Bradshaw et al. |
| 5,147,385 A | 9/1992 | Beck et al. |
| 5,199,939 A | 4/1993 | Dake et al. |
| 5,213,561 A | 5/1993 | Weinstein et al. |
| 5,292,321 A | 3/1994 | Lee |
| 5,354,257 A | 10/1994 | Roubin et al. |
| 5,370,608 A | 12/1994 | Sahota et al. |
| 5,380,282 A | 1/1995 | Burns |
| 5,383,856 A | 1/1995 | Bersin |
| 5,409,483 A | 4/1995 | Campbell et al. |
| 5,415,635 A | 5/1995 | Bagaoisan et al. |
| 5,415,654 A | 5/1995 | Daikuzono |
| 5,417,689 A | 5/1995 | Fine |
| 5,419,760 A | 5/1995 | Narciso, Jr. |

(List continued on next page.)

OTHER PUBLICATIONS

Angelini, et al., "Distention promotes platelet and leukocyte adhesion and reduces short–term patency in pig arterio-venous bypass grafts," *J. Thorac. Cardiovasc. Surg.*, 99:433–439 (1990).

Angelini, "Time–course of medial and intimal thickening in pig venous arterial grafts: relationship to endothelial injury and cholesterol accumulation". *J. Thorac. Cardiovasc. Surg.*, 103:1093–1103 (1992).

Aust, "Saphenous Vein Graft as a Conduit for Hepatic Artery Catheters in Anomalies of the Hepatic Arterial System," *Surgery*, 100(1):581–583 (1986).

(List continued on next page.)

*Primary Examiner*—Samuel G. Gilbert
(74) *Attorney, Agent, or Firm*—Bruce D. Gray; Kristin D. Mallatt; Kilpatrick Stockton LLP

(57) ABSTRACT

Fibrointimal proliferation, neointimal hyperplasia and other vascular lesions or injuries are reduced by ex vivo irradiation of the autologous coronary bypass conduit, especially the saphenous vein, as an adjunct in cardiovascular surgery or other treatment, in anyone of a variety of suitable devices.

11 Claims, 8 Drawing Sheets

U.S. PATENT DOCUMENTS

| | | | |
|---|---|---|---|
| 5,421,955 A | 6/1995 | Lau et al. | |
| 5,429,634 A | 7/1995 | Narciso, Jr. | |
| 5,441,516 A | 8/1995 | Wang et al. | |
| 5,449,373 A | 9/1995 | Pinchasik et al. | |
| 5,458,615 A | 10/1995 | Klemm et al. | |
| 5,484,384 A | 1/1996 | Fearnot | |
| 5,496,271 A | 3/1996 | Burton et al. | |
| 5,643,712 A | 7/1997 | Brasile | |
| 5,707,332 A | 1/1998 | Weinberger | |
| 5,792,603 A | 8/1998 | Dunkelman et al. | |
| 5,833,593 A | 11/1998 | Liprie | |
| 5,910,101 A | 6/1999 | Andrews et al. | |
| 6,095,966 A | 8/2000 | Chornenky et al. | |
| 6,374,866 B1 * | 4/2002 | Love et al. | 140/71 R |
| 6,387,116 B1 * | 5/2002 | McKenzie et al. | 623/1.1 |
| 6,419,625 B1 * | 7/2002 | Smith | 600/36 |

OTHER PUBLICATIONS

Batayias, et al., "The spectrum of pathological changes in aorticocoronary *saphenous* vein grafts" *Cardiovasc. Surg.* 56(Supp 2, Circulation):II 18–22 (1977).

Boerboom, et al., "Histologic, morphometric and biochemical evolution of vein bypass grafts in a nonhuman primate model," *J. Thorac. Cardiovasc. Surg.*, 99:97–106 (1990).

Boerboom, et al., "Histologic, morphometric and biochemical evolution of vein bypass grafts in a nonhuman primate model;". *J. Thorac. Cardiovasc. Surg.* 99:107–112 ( 1990).

Bottcher, et al., "Endovascular irradiation–a new method to avoid recurrent stenosis after stent implantation in peripheral arteries: technique and preliminary results" *Int. J. Radiat. Oncol. Biol. Phys.* vol. 29: 183–186 (1994).

Brody, et al., "Histologic Fate of the Venous Coronary Artery Bypass In Dogs," *American Journal of Pathology,* 66:111–130 (1972).

Chesebro, et al., "A Platelet–Inhibitor–Drug Trial in Coronary–Artery Bypass Operations: Benefit of Perioperative Dipyridamole and Aspirin Therapy on Early Postoperative Vein–Graft Patency," *New England Journal of Medicine,* 307(2):73–78 (Jul. 8, 1982).

Chesebro, et al., "Drug trials in prevention of occlusion of aorta–coronary artery vein grafts," *J. Thorac. Cardiovasc. Surg.,* 83:90–93 (1982).

Chesebro, et al., "Effect of Dipyridamole and Aspirin on Late Vein–Graft Patency After Coronary Bypass Operations," *The New England Journal of Medicine,* 310(4):209–214 (Jan. 26, 1984).

Chesebro, "Platelet–inhibitor drugs before and after coronary artery bypass surgery and coronary angioplasty: The basis of their use, data from animal studies, clinical trial data, and current recommendations," *Cardiology.* 73:292–305 (1986).

Chesebro, et al., Does Dipyridamole Plus Aspirin Affect Aortocoronary Vein Graft Narrowing Over the First Postoperative Year? *Abstracts of the 57th Scientific Sessions,* II–105:417 (undated)

Choi, et al., "Regional chemotherapy through a *saphenous* vein graft for the treatment of head and neck cancers," *Cancer,* 60(7):1432–1438 (1987).

Condado, et al., "Late Follow–Up After Percutaneous Transluminal Coronary Angioplasty (PTCA) and Intracoronary Radiation Therapy (ICRT), " *Discoveries in Radiation for Restenosis,* Presented by The Andreas Gruentzig Cardiovascular Center and The Department of Radiation Oncology of Emory University School of Medicine, J. W. Marroitt Hotel at Lenox, Atlanta, Georgia, Abstract 34 (Jan. 11–12, 1996).

Cox, et al., "Stranger in a strange land: the pathogenesis of *saphenous* vein graft stenosis woth emphasis on structural and functional differences between veins and arteries," *Prog. Cardiovasc. Dis.* 34:45–68 (1991).

Crocker, "Endovascular Gamma Irradiation in the Swine Model: the Emory Experience," *Discoveries in Radiation for Restenosis,* pp. 37–38 (Jan. 1996).

Dorland's Pocket Medical Dictionary, 24th edition, Dec. 1982, p. 226.

Falk, et al., "Thermal coronary angiography for intraoperative patency control of arterial and *saphenous* vein coronary artery bypass grapts: results in 370 patients," *J. Card. Surg.,* 10(2):147–160 (1995).

Fischell, et al., "Low–dose, B–particle emission from "stent" wire results in complete, localized inhibition of smooth muscle cell proliferation," *Circulation,* 90:2956–2963 (1994).

Fonkalsrud, et al., "Morphological evaluation of canine autogeneous vein grafts in the arterial circulation," *Surgery,* 253–264 (Aug. 1978).

Gillette, et al., "Response of aorta and branch arteries to experimental intraoperative irradiation" *Int. J. Radiat. Oncol. Biol. Phys.* 17:1247–1255 (1989).

Gillette, "Aortic wall injury following intraoperative irradiation" *Int. J. Radiat. Oncol. Biol. Phys.* 15:1401–1406 (1988).

Grondin, et al., "Coronary artery bypass grafting with *saphenous* vein," *circulation,* 79(Suppl I) I 24–9 (1989).

Hall, Eric J., *Radiobiology for the radiologist,* 4th ed. Philadelphia: J.B. Lippincott Company, (1994).

Ho, et al., "Regional Chemotherapy for recurrent squamous head and neck cancers through a *saphenous* vein interposition graft," *Arch. Otolaryngol. Head Neck Surg.,* 119(1):608–611 (1993).

Mohr, et al., "Thermal coronary angiography: a method for assessing graft patency and coronary anatomy in coronary bypass surgery," *Ann. Thorac. Surg.,* 47(3):441–449 (1989).

Kern, et al., "The pathology of surgically excised aortocoronary *saphenous* vein bypass grafts," *Am. J. Surg. Pathol.,* 5:491–6 (1981).

Kern, et al., "The intimal proliferation in aortic–coronary *saphenous* vein grafts" *Am. Heart J.* 84:771–77 (1972).

Kosuga, et al., "A study of reservoir implantation: Especially with *saphenous* vein graft catheterization," *Kurume Medical Journal,* 41(1):23–30 (1994).

Loop, et al., "Influence of the internal–mammary–artery graft on 10–year survival and other cardiac events," *N. Engl. J. Med.* 314:1–6 (1986).

Mazur, et al., "High dose rate radiation suppresses neointimal proliferation ion the stented and ballooned model of porcine restenosis" *Circulation.* 90(4): 3510, Abstract From the 67th Scientific Sessions, Dallas Convention Center, Dallas, Texas (Nov. 14–17, 1994).

Miller, et al., "Endothelium–dependent Responses in Autogenous Femoral Veins Grated into the Arterial Circulation of the Dog," *J. of Clinical Investigation,* 80:1350–1357 (1987).

Nahai, et al., "One-stage microvascular transfer of a *latissimus* flap to the sacrum using vein grafts," *Plast. Reconstr. Surg.*, 77(1–6):312–315 (1986).

Penny, et al., "Antithrombotic therapy for patients with cardiac disease," *Curr. Probl. Cardiol.* 13:425–513 (1988).

Popowski, et al., "High Dose Rate Brachytherapy for Prevention of Restenosis After Percutaneous Translyminal Coronary Angioplasia: Preliminary Dosimetric Tests of a New Source Presentation," *Int. J. Radiation Oncology Biol. Phys.*, 33(1):211–215 (1995).

Ramos, et al., "Histologic Fate and Endothelial Changes of Distended and Nondistended Vein Grafts," *Annals of Surgery*, 183(3):205–228 (Mar. 1976).

Rholl, et al., "Work in progress. Transcatheter thermal venous occlusion: a new technique," *Radiology*, 145(2):333–337 (1982).

Schwartz, et al., "Effect of external beam irradiation on neointimal hyperplasia after experimental coronary artery injury," *J. Am. Coll. Cardiol.*, 19:1106–13 (1992).

Sergeant, et al., "The return of clinically evident ischemia after coronary artery bypass grafting," *Eur. J. Cardiothorac. Surg.*, 5:447–57 (1991).

Smith, Robin A., "Potential Advantages of Treatment of Transplanted Saphenous Vein Aorto–Coronary Artery Bypass Grafts with Beta Irradiation to Prevent Graft Occlusion," *Int. J. Transplant*.

Storm, et al., "Autogenous vein bypass grafts: Biological effects of mechanical dilation and adventitial tripping in dogs," *Surgery*, (77)261–267 (1975).

Szilagyi, et al., "Biological Fate of Autogenous Vein Implants as Arterial Substitutes," *Annals of Surgery*, 178:232–246 (1973).

Verin, et al., "Intraarterial beta irradiation for prevention of post–angioplasty restenosis" *J Invasc Cardiol.* 7:1, Abstract TCT–45 (1995).

Verin, et al., "Endovascular Beta Radiation in The Atheroscerotic Rabbit Model," *Discoveries in Radiation for Restenosis*, pp. 51–54 (Jan. 1996).

Waksman, et al., "Endovascular Low–Dose Irradiation Inhibits Neointimal Formation After Coronary Artery Balloon Injury in Swine," *Circulation*, 91(5):1533–1539 (Mar. 1, 1995).

Waksman, et al., "Effects of endovascular irradiation in a swine model of restenosis after angioplasty". *J. Am. Coll. Cardiol.* 1A–484A; Abstract 831–3 (1994).

Waksmna R, Robinson KA, Crocker IR, Gravanis MB, Cipolla GD, King SB. "Endovascular low–dose irradiation inhibits neointima formation after coronary artery balloon injury on swine" *Circulation*, 91:1533–1539 (1995).

Wiedermann. et al., "Intracoronary irradiation markedly reduces restenosis after balloon angioplasty in a porcine model," *J. Am. Coll. Cardiol.* 23:1491–1498 (1994).

Cole–Parmer Instrument Company catalogue, pp. 310–317, 320, 321, 730 (date unknown).

* cited by examiner

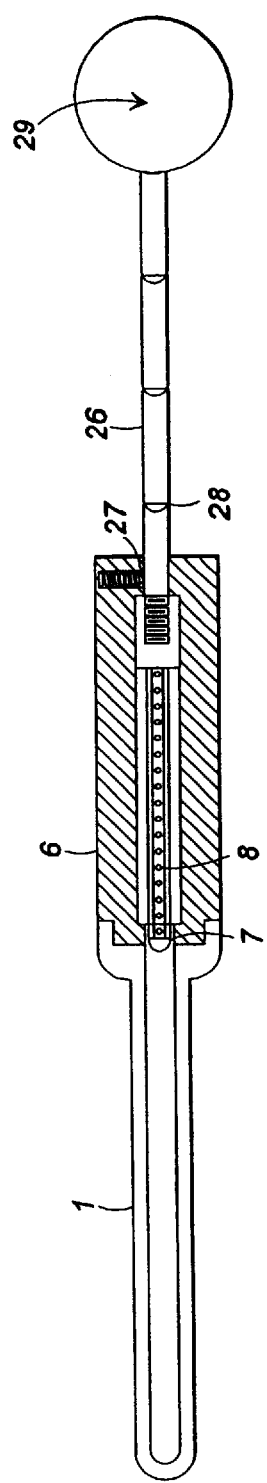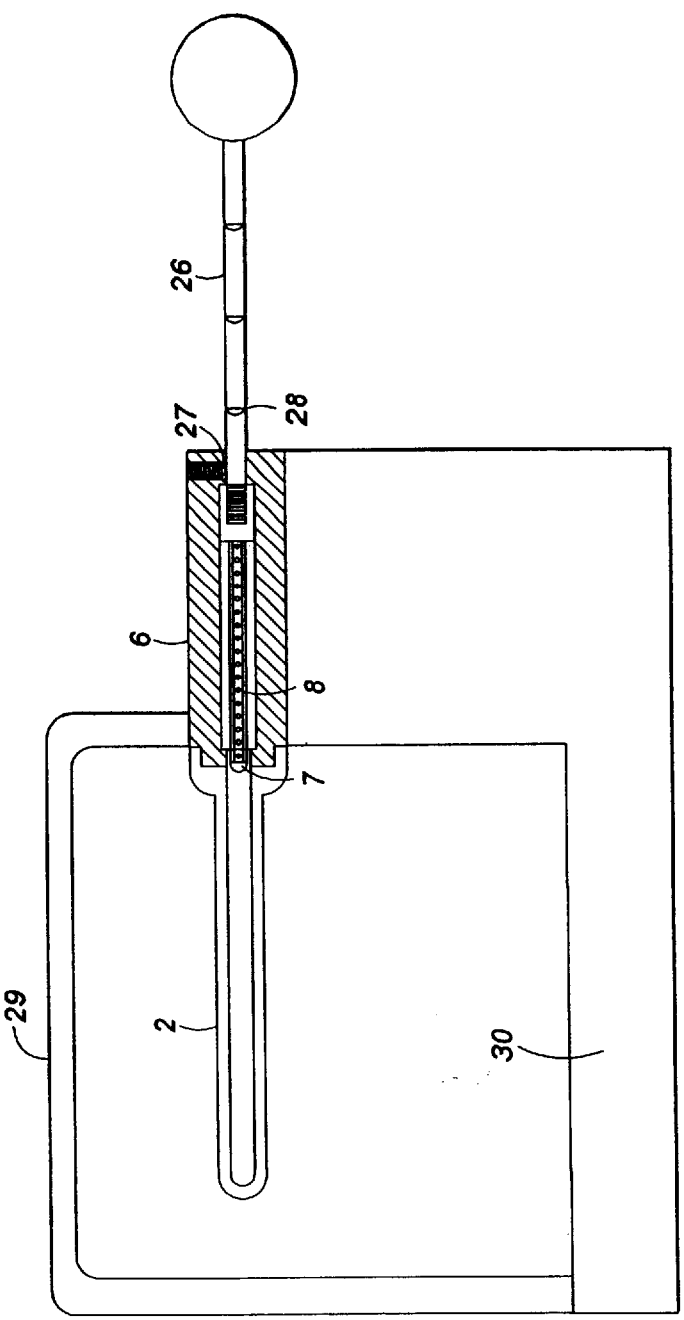
FIG. 7
FIG. 8

METHODS AND DEVICES FOR EX VIVO IRRADIATION OF AUTOLOGOUS CORONARY BYPASS CONDUIT

This application is a continuation of U.S. Ser. No. 08/999,290, filed Dec. 29, 1997, entitled "Methods and Devices for ex vivo Irradiation of Autologous Coronary Bypass Conduit," now allowed as U.S. Pat. No. 6,419,625 which claims benefit of No. 60/035,739 filed Jan. 3, 1997 which claims benefit of No. 60/040,293 filed Feb. 11, 1997.

BACKGROUND OF THE INVENTION

It is known that the human body's healing response to injury typically includes the formation of what is commonly called scar tissue. A microscopically similar response also occurs within the transplanted vascular tissue of a person following transplantation of the saphenous vein into the coronary artery or peripheral vascular circulation to serve as a bypass.

One area of the vascular system of particular concern with respect to such injuries is saphenous veins that are used to provide bypass conduits for obstructed coronary arteries and also for obstructed peripheral arteries. Partial and even complete blockage of saphenous vein bypass grafts by the sequential and overlapping processes of thrombosis (formation of blood clots), fibrointimal hyperplasia (smooth muscle cell overgrowth) or formation of an atherosclerotic plaque upon the inner lining of the already thickened saphenous vein segment is a well known and frequent medical problem following coronary artery bypass grafting.

Occlusion of coronary artery bypass grafts occurs in more than fifty percent of saphenous vein grafts by the time the graft is ten years old, affecting the majority of patients with saphenous vein bypass grafts.

In conventional treatment, such blockages may be treated using atherectomy devices, which mechanically remove the plaque; hot or cold lasers, which vaporize the plaque; stents, which hold the artery open; and other devices and procedures which have the object of allowing increased blood flow through the bypass conduit. The most common such procedure is the percutaneous transluminal coronary angioplasty (PTCA) procedure, more commonly referred to as balloon angioplasty. In this procedure, a catheter having an inflatable balloon at its distal end is introduced into the coronary artery or saphenous vein bypass graft, the uninflated balloon is positioned at the stenotic site and the balloon is inflated. Inflation of the balloon disrupts and flattens the plaque against the vessel wall, and stretches the arterial or venous wall, resulting in enlargement of the intraluminal passageway and increased blood flow. After such expansion, the balloon is deflated and the balloon catheter removed.

However, all of the above conventional remedies for vascular occlusion are performed after the vein is sewn into the coronary artery system and after the problem of vascular occlusive disease has developed and become a problem for the patient. By contrast, the present invention provides methods and devices to prevent such blockage from occurring, by irradiation of the bypass graft during the bypass graft surgical procedure.

Smooth muscle cell migration and proliferation are stimulated in several ways during transplant of vascular tissue such as saphenous veins, including mechanical trauma, and baurotrama. Such stimulation also occurs from denudation of the endothelium, and from mitogenic proliferative factors, such as platelet-derived growth factor, fibroblast growth factors, and epidermal growth factor. These influences initiate the body's own natural repair and healing process. During this healing process, vascular smooth muscle cells migrate into the intima and prolferate. The formation of scar tissue by smooth muscle proliferation, also known as fibrointimal hyperplasia, is believed to be a major contributor to the occlusion of saphenous vein bypass grafts following placement of vein grafts into the aortocoronary circulation.

Prior efforts to inhibit occlusion of saphenous vein grafts have included optimal antiplatelet therapy with the combination of aspirin and dipyridamole, which reduced the rate of occlusion from about 25% at one year to about 11%. However, the improvement relating to the prevention of thrombosis had no identifiable beneficial effect upon the process of fibrointimal proliferation. Fibrointimal proliferation results in about 25% lumenal narrowing by the end of one year in all vein graft segments.

Although radiation therapy has shown promise, particularly in inhibiting neotintimal hyperplasia within the in vivo arterial circulation, the devices available for delivery of radiation sources have been limited to treating a segment of vascular tissue within the patient, and have not been applied to treatment of vascular tissue being transplanted from one site of the body to another while it is outside of the patient's body.

The present invention includes ex vivo methods of treating vascular tissue, e.g., saphenous vein coronary artery bypass grafts, with endovascular irradiation, particularly beta irradiation. This method is particularly suitable for ex vivo applications. The inventor has also developed devices suitable for such methods, including sterile sleeves for endovascular positioning of the radiation source, housings for the radiation sources, and a radiation seed safe module for the purpose of shielding and storing the radiation source, said module containing radiation pellets for insertion into the sleeve lumen or cavity.

The methods and devices of the present invention are suitable for reducing fibrointimal proliferation or neointimal hyperplasia, vascular lesions that commonly occur in the treatment of cardiovascular disease, e.g. balloon angioplasty, coronary bypass surgery. The present invention is also suitable for achieving a clinically significant decrease in the morbidity and mortality resulting from SVG occlusions, particularly in view of the large number of patients at risk. About 220,000 patients undergo each year coronary artery bypass surgery with a saphenous vein as the bypass conduit, of which about 22,000 would substantially benefit from the methods and devices of the present invention.

BRIEF DESCRIPTION OF THE INVENTION

The present invention is directed to devices and methods for delivering one or more treating elements, such as a radiation source, into or outside of a suitable sleeve or elongated means, upon which is placed a segment of a suitable graft, e.g., saphenouse vein. The vein has been removed from the patient's leg or arm and divided into one or more tubular segments for use as bypass material. The vein is mounted on the sleeve or elongated means. It is then subjected to radiation effective to reduce or inhibit overgrowth of vascular repair tissue, by exposure to a radiation source within the lumen of the graft or outside of the graft. Having irradiated the graft, it is then implanted back into the patient before finishing the bypass surgery.

Methods of irradiating saphenous coronary bypass conduits is also disclosed, including a suitable apparatus for ex vivo applications. One preferred method and apparatus of the present invention involves coronary bypass surgery with an autologous saphenous vein graft, using $^{90}$Sr seeds as a beta radiation source.

BRIEF DESCRIPTION OF THE DRAWINGS

FIG. 7 schematically shows is a sterile sleeve attached directly, without adaptor, to a radiation seed safe module with plunger for insertion of radiation seeds through the lumen of the sleeve, according to a preferred embodiment of the present invention.

FIG. 8 schematically shows the device of FIG. 7 with housing acting as a radiation shield.

Figure 1:
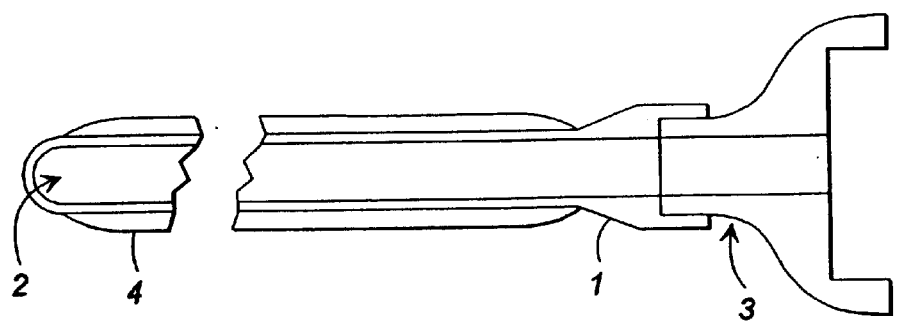
FIG. 1 schematically shows a sterile sleeve 1 with adaptor 3, according to a preferred embodiment of the present invention.

| ABBREVIATIONS AND DEFINITIONS | |
|---|---|
| CABG | Coronary Artery Bypass Graft |
| Conduit graft | Vessel graft, which is a vein or artery |
| FIH | Fibrointimal Proliferation, also known as Neointimal Hyperplasia. An exuberant or excessive growth of reparative tissue in the vessel in response to injury. |
| Gy | Gray, a unit of absorbed radiation dose, i.e. the absorbed dose when the energy per unit mass imparted to matter by ionizing radiation is 1 joule per kilogram. $10^{-2}$ Gy = rad (rd). |
| IMA | Internal Mammary Artery |
| NIH | Neointimal Hyperplasia, also known as Neointimal Proliferation. |
| PTCA | Percutaneous Transluminal Coronary Angioplasty |
| SVG | Saphenous Vein Graft |

DETAILED DESCRIPTION OF THE INVENTION

The present invention relates to methods and devices for inhibition of overgrowth of vascular tissue, e.g., fibrointimal proliferation or neointimal hyperplasia, in transplanted vascular tissue. The treatments described in the present invention occur during the surgical grafting procedure, but their effect is often not detected clinically for many months after successful completion of the surgery. The present invention also relates to revascularization procedures such as bypass grafting of the femoral artery to the popliteal artery, aortofemoral bypass grafting procedures utilizing transplanted autologous vascular tissues, such as the autologous saphenous vein.

The present invention relates to a method of reducing overgrowth of vascular repair tissue, e.g., fibrointimal proliferation or neointimal hyperplasia, in autologous coronary bypass conduit grafts, comprising the steps of:

(a) providing a graft harvested ex vivo from a mammal;
(b) subjecting the graft to irradiation with a dose effective for reducing fibrointimal proliferation or neointimal hyperplasia, to give a treated graft; and
(c) surgically implanting the treated graft into same mammal.

In one embodiment of the method of the present invention, the coronary bypass conduit graft is removed from the long saphenous vein, the short saphenous vein, the cephalic vein, the brachiocephalic vein, or radial artery.

In another embodiment of the method of the present invention, the irradiation is beta irradiation from within the lumen of the graft.

In another embodiment of the method of the present invention, the irradiation is X irradiation from a micro X-ray source within the lumen of the graft.

In another embodiment of the method of the present invention, the irradiation is from the gamma emitting radionuclide $^{125}$I.

In another embodiment of the method of the present invention, the mammal is a human.

In another embodiment of the method of the present invention, the dose is limited to a range of between about 1.0 Gy and about 60.0 Gy.

In another embodiment of the method of the present invention, the dose is limited to a range of between about 3.0 Gy and about 30.0 Gy.

In another embodiment of the method of the present invention, the dose is limited to a range of between about 6.0 Gy and about 20.0 Gy.

In another embodiment of the method of the present invention, the radiation source is $^{90}$Sr.

One specific embodiment of the present invention is a method of reducing fibrointimal proliferation or neointimal hyperplasia in autologous coronary bypass vein grafts, comprising the steps of:
 (a) providing a vein harvested ex vivo from a human, said vein selected from the long saphenous vein and the short saphenous vein;
 (b) subjecting the vein to beta irradiation from within the lumen of the vein, with a dose effective for reducing fibrointimal proliferation or neointimal hyperplasia, said dose ranging from between about 6.0 Gy and about 20.0 Gy of $^{90}$Sr, to give a treated vein; and
 (c) surgically implanting the treated vein into same human.

The present invention also relates to a device for irradiating ex vivo autologous coronary bypass conduit grafts of a mammal, comprising
 (a) a sterile sleeve insertable ex vivo into the lumen of the graft; and
 (b) a radiation source capable of delivering a dose effective for reducing fibrointimal proliferation or neointimal hyperplasia in the graft, said source insertable into said sleeve for endovascular delivery of the radiation dose to the graft.

In one embodiment of the device of the present invention, the coronary bypass conduit graft is removed from the long saphenous vein, the short saphenous vein, the cephalic vein, the brachiocephalic vein, or radial artery.

In another embodiment of the device of the present invention, the radiation source produces beta irradiation.

In another embodiment of the device of the present invention, the radiation is X rays from a micro X-ray source.

In another embodiment of the device of the present invention, the radiation source is the gamma emitting radionuclide $^{125}$I.

In another embodiment of the device of the present invention, the mammal is a human.

In another embodiment of the device of the present invention, the radiation source delivers a dose of between about 1.0 Gy and about 60.0 Gy.

In another embodiment of the device of the present invention, the radiation source delivers a dose of between about 3.0 Gy and about 30.0 Gy.

In another embodiment of the device of the present invention, the radiation source delivers a dose of between about 6.0 Gy and about 20.0 Gy.

In another embodiment of the device of the present invention, the radiation source is $^{90}$Sr.

The present invention also relates to a device for irradiating ex vivo an autologous coronary bypass vein graft in a human, comprising
 (a) a sterile sleeve insertable ex vivo into the lumen of the vein graft; and
 (b) a radiation source capable of delivering a dose effective for reducing fibrointimal proliferation or neointimal hyperplasia in the vein graft, said source comprising radiation seeds of $^{90}$Sr, said source insertable into said sleeve for endovascular delivery of the radiation dose to the vein graft, said dose ranging from between about 6.0 Gy and about 20.0 Gy.

The present invention also relates to a second device for irradiating ex vivo an autologous coronary bypass conduit graft of a mammal, comprising
 (a) a sterile sleeve for holding ex vivo the graft during its irradiation, wherein the sleeve is insertable ex vivo into the graft lumen;
 (b) a radiation seed safe module attached, with or without fixed or detachable adaptor means, to the sleeve with locking or screwing means, said module containing a radiation source capable of being driven into and through the lumen of the sterile sleeve to provide endovascular delivery of a radiation dose to the graft, said radiation dose suitable for reducing fibrointimal proliferation or neointimal hyperplasia in the graft; and
 (c) a radiation shield attached at or near the junction of the sleeve and the radiation seed safe module.

In one embodiment of the second device of the present invention, the coronary bypass conduit graft is removed from the long saphenous vein, the short saphenous vein, the cephalic vein, the brachiocephalic vein, or radial artery.

In another embodiment of the second device of the present invention, the radiation source produces beta irradiation.

In another embodiment of the second device of the present invention, the radiation is X-rays from a micro X-ray source.

In another embodiment of the second device of the present invention, the radiation comes from the gamma emitting radionuclide $^{125}$I.

In another embodiment of the second device of the present invention, the mammal is human.

In another embodiment of the second device of the present invention, the radiation source comprises radiation seeds of $^{90}$Sr.

In another embodiment of the second device of the present invention, the radiation dose is limited to the range between about 1.0 Gy and about 60.0 Gy.

In another embodiment of the second device of the present invention, the radiation dose is limited to the range between about 3.0 Gy and about 30.0 Gy.

In another embodiment of the second device of the present invention, the radiation dose is limited to the range between about 6.0 Gy and about 20.0 Gy.

The present invention also relates to a device for beta irradiating ex vivo an autologous vein graft of a human, comprising
 (a) a sterile sleeve for holding ex vivo the graft during its irradiation, wherein the sleeve is insertable ex vivo into the graft lumen;
 (b) a radiation seed safe module attached, with or without fixed or detachable adaptor means, to the sleeve with locking or screwing means, said module containing a radiation source comprising one or more radiation seeds of $^{90}$Sr capable of being driven into and through the lumen of the sleeve to provide endovascular delivery of a radiation dose to the graft, said radiation dose suitable for reducing fibrointimal proliferation or neointimal hyperplasia in the graft, said radiation dose between about 8.0 Gy and about 20.0 Gy; and
 (c) a radiation shield attached at or near the junction of the sleeve and the radiation seed safe module.

The present invention also relates to a third device for irradiating ex vivo autologous coronary bypass conduit grafts of a mammal, comprising
 (a) a sterile slender elongated means insertable ex vivo into the lumen of the graft, for the purpose of mounting and positioning the graft;
 (b) a cylinder with one or more attached radiation sources, said elongated means with mounted graft insertable into the inside of the cylinder for exovascular delivery of the radiation dose to the graft, said radiation sources capable of delivering a dose effective for reducing fibrointimal proliferation or neointimal hyperplasia in the graft.

FIG. 1 shows schematically a sterile disposable sleeve 1, according to a preferred embodiment of the present invention. Sleeve 1 may be formed of any desired material, including plastic or other polymeric material, preferably plastic. The sleeve 1 is optionally covered with balloon 4. The sleeve 1 without balloon varies between about 1 and about 8 mm in outer diameter. It may be inserted by the surgeon into the coronary bypass conduit, e.g., the saphenous vein segment. The balloon 4 is placed to account for varying inner diameters of the bypass conduit lumen, in order to enhance uniform irradiation of the graft. The balloon 4 can be inflated according to the size of the graft lumen, and the pressure within the balloon can optionally be monitored with a conventional manometer. The sleeve 1 is sealed closed at one end and is open at the other so that the shielded radiation, e.g., strontium, source can be inserted into the sleeve after the bypass conduit graft is placed upon it. The sleeve 1 can be screw-locked (luer lok type) if desired into a sterile 1.2 cm thick clear plastic "test-tube" structure that protects the vein during the procedure, and attenuates any beta particles that pass through the vein segment during the radiation treatment (not shown). Optionally, the irradiation procedure can be performed with a hinged clear plastic hood 29 that attenuates beta rays, such as that exemplified in FIG. 8. The clear plastic hood 29 is typically at least about 1.2 cm thick.

Lumen 2 of the sleeve 1 is a hollow cavity inside of the sleeve 1, with the purpose of providing a way to insert, inside the vein, a radiation source, such as radiation seeds, for endovascular delivery of radiation. Typically lumen 2 is a cavity with a uniform inner diameter, formed, for example, by drilling at one end of an elongated means to form the sleeve 1.

Figure 2A:
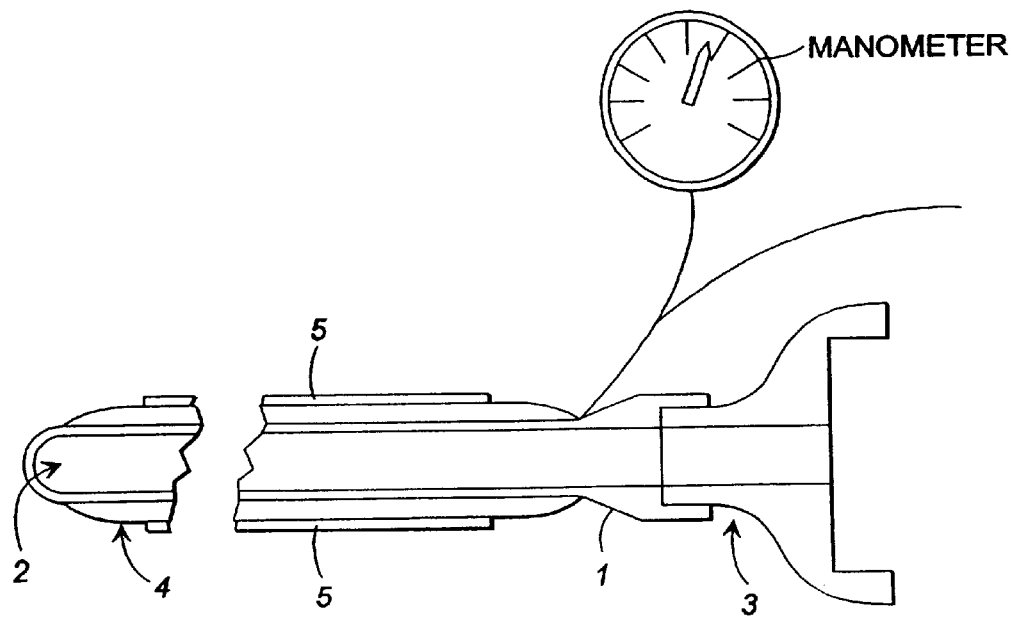
FIG. 2A schematically shows a sterile sleeve of FIG. 1 with a graft in position for endovascular delivery of radiation.

Placement of a graft 5 on the plastic sleeve 1 is shown schematically in FIG. 2A, according to a preferred embodiment of the invention. The graft is shown in cross-section. A pressure measuring device, e.g., a manometer, is also shown for balloon 4. It will be understood from this and other figures that the size and pressure of the balloon are adaptable to the size of the particular graft about to be reimplanted into its autologous host. Alternatively, the balloon 4 may be manufactured to inflate to a predetermined external diameter and length. In some cases, a balloon is not necessary to the method and procedure of the present invention, e.g., a solid plastic rod with lumen or cavity for radiation source may be sufficient.

Figure 2B:
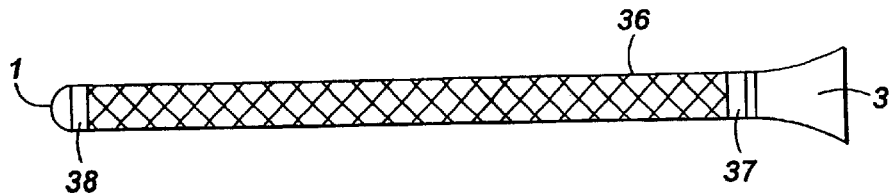
FIG. 2B schematically shows a sterile sleeve of FIG. 1 with mesh instead of a balloon, according to a preferred embodiment of the present invention.
Figure 2C:
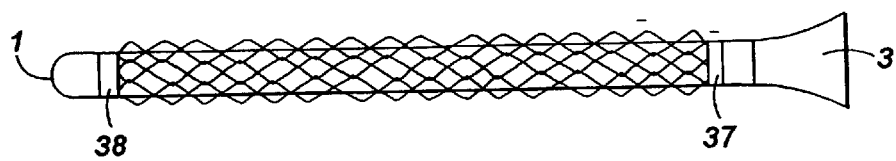
FIG. 2C schematically shows a sterile sleeve of FIG. 2B with mesh expanded to fit a vein graft to be placed thereon, according to a preferred embodiment of the present invention.
Figure 2D:
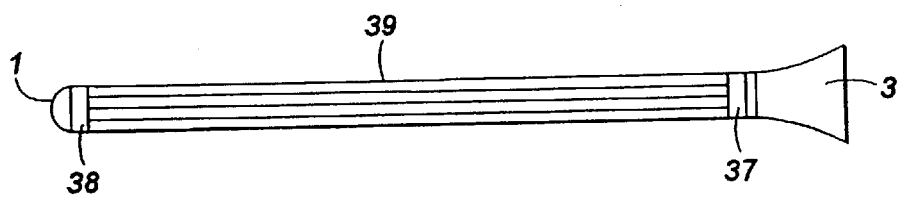
FIG. 2D schematically shows a sterile sleeve of FIG. 1 with filaments intended to bow out to fit a vein graft to be placed thereon, according to a preferred embodiment of the present invention.
Figure 2E:
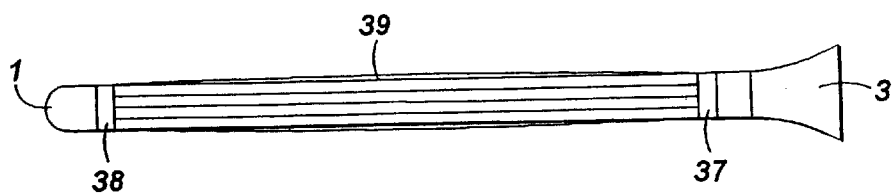
FIG. 2E schematically shows a sterile sleeve of FIG. 2D with filaments bowed out, according to a preferred embodiment of the present invention.

Instead of a balloon, appropriate placement of mesh or filaments are readily employed to position the vein to receive a substantially uniform radiation dose. For example, FIG. 2B schematically shows, according to one embodiment of the present invention, a sterile sleeve 1 with mesh 36 bounded by a fixed collar 37 and a slidable collar 38. To expand the mesh 36, the slidable collar 38 is moved toward the fixed collar 37. An illustration of an expanded mesh is schematically shown in FIG. 2C, according to one preferred embodiment of the present invention, with slidable collar 38 moved away from the distal end of sterile sleeve 1. To give an example of the filaments, FIG. 2C schematically shows, according to one embodiment of the present invention, a sterile sleeve 1.

Figure 3:
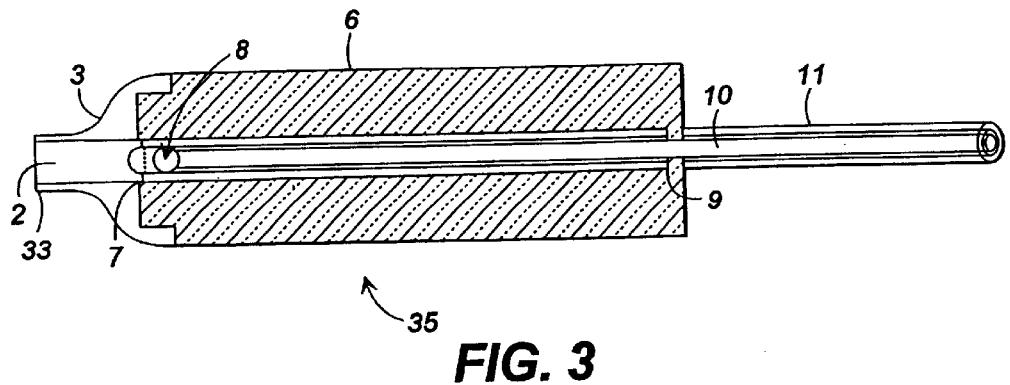
FIG. 3 schematically shows a radiation seed safe module with adaptor, according to a preferred embodiment of the present invention.

A radiation seed safe module 34, depicted schematically in FIG. 3, houses radiation seeds 8 in a detachable safe 6, prior to endovascular delivery of the radiation seeds 8 into the lumen 2 of the sleeve 1. See also FIG. 2. An end cap 7, which can be metallic or formed of other desired material, protects handlers from unwanted irradiation when the adaptor 3 or other attachment means is removed. An internal source stop 9 prevents retraction of the radiation source, e.g., seeds, beyond and outside of the detachable safe 6. Within the lumen 2 of the detachable safe 6, is an outer cable sleeving 11, and an inner cable 10, typically epoxied. The adaptor 3 when present, may have a threaded fitting 33 for attachment to the sterile sleeve 1, or it may lock onto the sterile sleeve 1.

Figure 4:
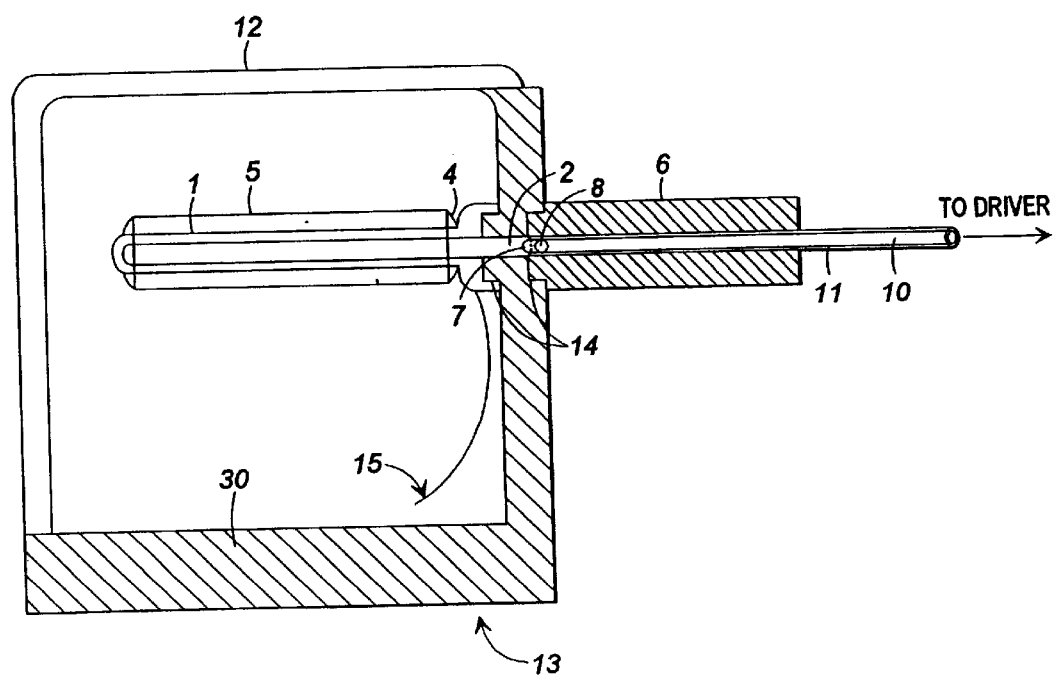
FIG. 4 schematically shows a total assembly, according to a preferred embodiment of the present invention, comprising sterile sleeve, with graft in place, the radiation seed safe module, radiation shield, with continuous inner lumen for driving radiation seeds into the lumen of the sleeve.

There are a variety of ways to attach sleeve 1 to the detachable safe 6. The sleeve 1 can be directly attached to the detachable safe 6 as illustrated schematically in FIGS. 7 and 8. Alternatively, the sleeve 1 can be attached to the base and pedestal 30, to which is attached the detachable safe 6, such that a lumen 2 forms a continuous passageway to allow insertion of radiation seeds into the lumen 2 of the sleeve 1, as illustrated in FIG. 4. Another means of attachment is with an adaptor 3 that is fixed or detachable, as illustrated in FIGS. 1–3. The attachment means in each such situation includes, but is not limited to, any permanent or detachable fitting, such as a threaded fitting, screw lock, luer lok, luer slip, John Guest® Quick Disconnect Fitting, Keck® connector, a barbed fitting, a flared fitting, a combination of a flared female end and male end, an Asti Teflon® connector, a loose collar capable of tightening the junction when screwed tight, a keyed fitting with one or more pins, a snap lock, and the like.

The radiation shield 12 can serve several other uses during the procedure. The radiation shield 12 can contain niches for thermolucent dosimeter diodes or for scintillation dosimeters (not shown) for the measurement of dose at the surface to provide a measure of irradiation that is transmitted through the vein. Such an arrangement provides an indirect measure of the dose absorbed by the vein FIG. 4 schematically shows a cross-section of an assembled device 13, according to a preferred embodiment of the present invention, with its component parts. The sleeve 1 with graft 5 is shown attached to a base and pedestal 30, with housing 12 serving as a radiation shield. Base and pedestal 30 is made of any desired material. Housing 12 is made of any desired material, preferably clear plastic. A tube 15 to an air inflator (not shown) provides means to inflate balloon 4. On the outside of the housing 12 is the radiation safe seed module 34 with detachable safe 6, end cap 7, outer cable sleeving 11, inner cable 10 and exemplary radiation seed 8. The lumen 2 forms a continuous passageway from the distal end of the detachable safe 6, which connects to the driver (not shown), through the base and pedestal 30 and into the sleeve 1. The inner cable 10 with radiation seeds 8 at or near its tip is driven into the lumen 2 of the sleeve 1, to deliver a radiation dose to graft 5. Typically, appropriate dosing can be achieved by one pass of the inner cable 10 with radiation seeds 8 into and out of the lumen 2 of the sleeve 1. When dosing is complete, the inner cable 10 is withdrawn from the lumen 2 of the sleeve 1 into the lumen 2 of the detachable safe 6. The graft at this point has been suitably irradiated and is ready for removal by the surgical staff for reimplanting in the patient.

Figure 5:
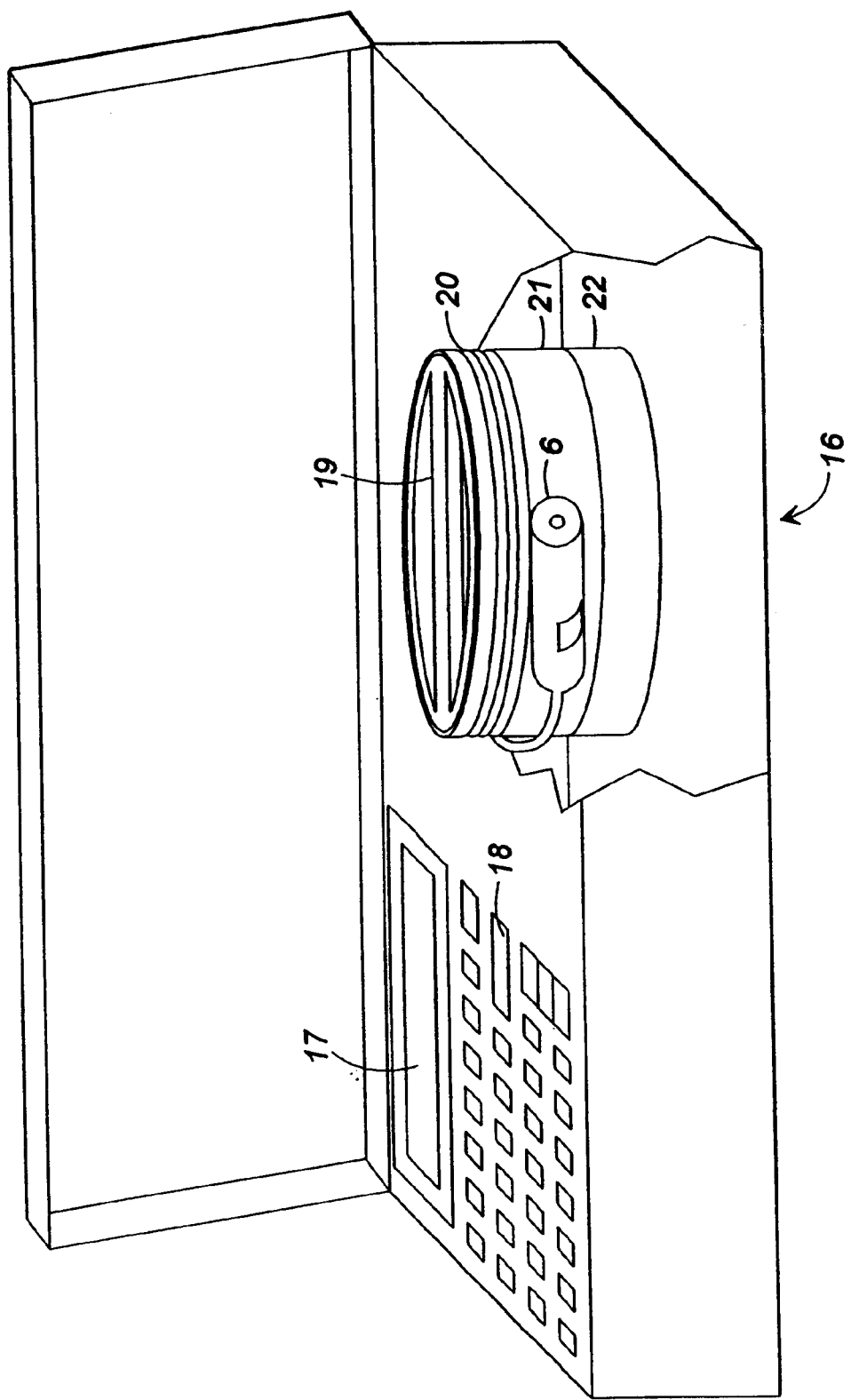
FIG. 5 schematically shows a beta source control device, according to a preferred embodiment of the present invention, with sleeve in place.

The beta source control device 16 of FIG. 5 exemplifies an electronic apparatus for automating the methods and devices of the present invention. Related afterloading devices suitable for different uses are disclosed and claimed in U.S. Pat. No. 5,103,395, herein incorporated by reference. The device 16 has the detachable safe 6 with attached cable and sheathing 20 wound around a drive cable capstand 21, which is rotatably driven by a drive stepping motor 22 for insertion and withdrawal of radiation source (not shown) into the sleeve 1 with graft 5 (not shown). An emergency retract handle 19 provides manual control of the endovascular delivery system of the present invention. A liquid crystal display readout 17 with data entry and control panel 18 are also set forth in FIG. 5.

Figure 6:
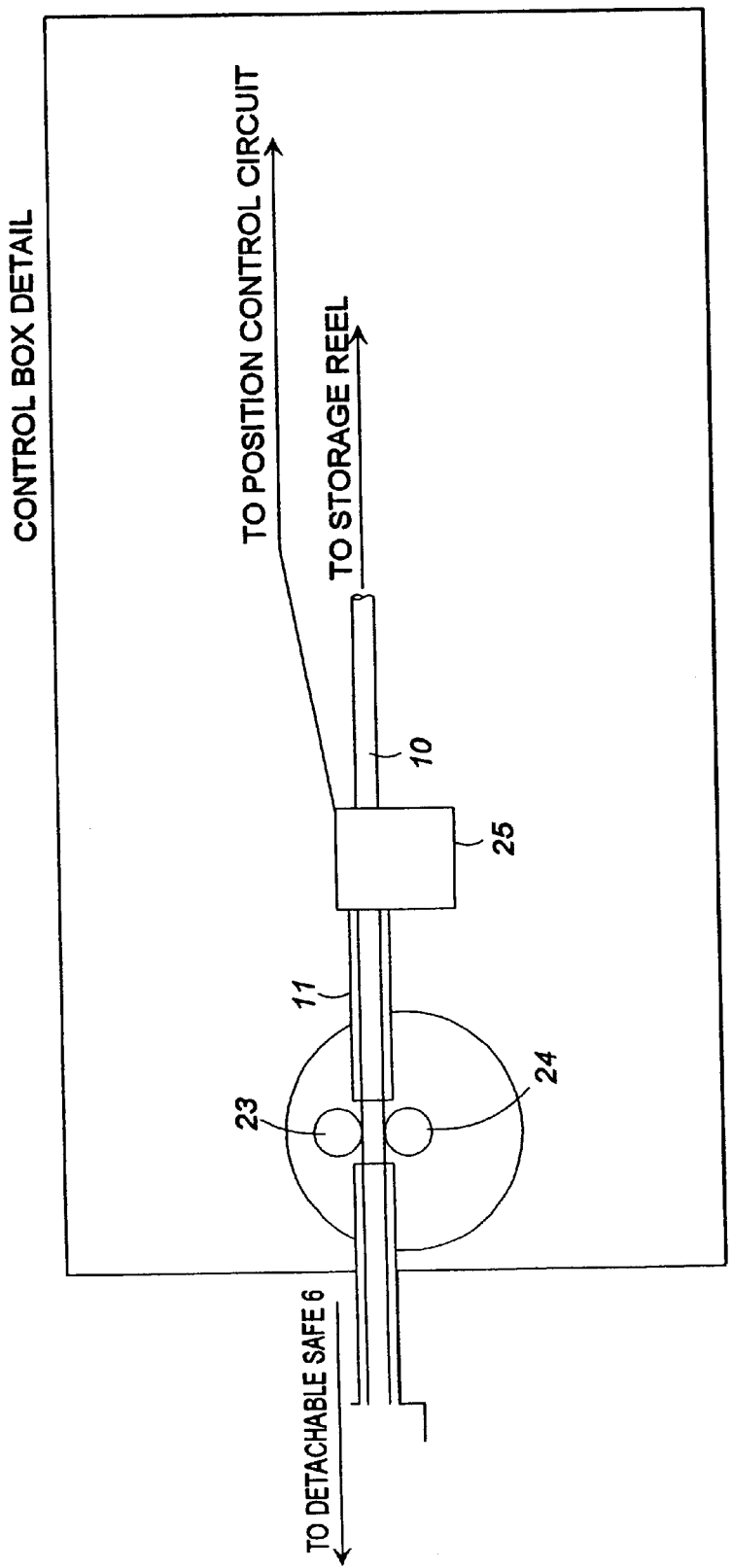
FIG. 6 schematically shows one form of a control unit or control box for positioning radiation pellets in ex vivo applications, according to a preferred embodiment of the present invention.

The control box for driving or inserting radiation seeds into the lumen of the sleeve is set forth in FIG. 6. The inner cable 10, which contains radiation seeds 8 (shown, for example, in FIGS. 3 and 4) is driven by a cable driver pinion 24 and motor, into and out of the lumen 2 of the sleeve 1 (not shown). Inner cable 10 is secured by outer cable sleeving 11. Inner cable 10 is held in place against the cable driver pinion 24 by a pinch idler 23. Pinch idler 23 rotates freely as the inner cable 10 is moved. Encoder 25 monitors the position of the inner cable 10 and is part of the position control circuit.

Using the radiation seed safe module attached to a computer-controlled stepping motor for the purpose of pushing or driving via cable, cam or high precision gear-driven telescoping device, such as is used to telescope a cameral lens, the source train of $^{90}Sr$ seeds, wire, or a single high-intensity source delivers the dose of irradiation in a more precisely controlled and more accurate manner than by manual manipulation. One illustration of this apparatus is schematically shown in FIGS. 5 and 6. The computer-controlled stepping motor prevents undesirable irradiation occurring during extrusion and retraction of the source train, which would add a small level of dose inhomogeniety along the length of the treated vessel graft. The stepping motor may be connected to the push-rod by a cam or a inner cable 10.

The inner cable 10 is on a spool within the unit containing the drive stepping motor 12. The outer cable sleeving 11 is uncoiled out of the motor module to be attached to the radiation seed safe module. (The radiation seed safe module may also be kept within the central unit with only a connector at the end of the outer cable sleeving 11). The drive stepping motor is a high speed, high precision device to deliver the radiation dose, by driving a spool of hard metal wound about which the inner cable is coiled. The inner cable extends into the outer cable sleeving and can be optionally attached to the end of the radiation source train (not shown) within the radiation seed safe module. The radiation seed safe module can be made so that the inner cable connects to the source train by screw lock or permanently fixed, or other conventional attachment means.

A variety of safety features are readily added to the devices of the present invention. In one model with a permanently attached radiation seed safe module, the radiation seed safe module can be machined so that the exit is smaller than the strontium seed casing so it cannot be retracted beyond the safe, e.g., an internal source stop 9 of FIG. 3. An encoder monitors the position of the inner cable and is part of the position control circuit. A screw clamp at each end of the radiation seed safe module prevents the radiation source from leaving the radiation seed safe module between treatments. Another interlock within the radiation seed safe module prevents accidental extrusion of the seeds until correctly connected. The drive stepping motor has a key that must be turned to the "on" position before it will drive the inner cable into and through the lumen of the sterile sleeve. The control panel also has a mechanical key control to prevent accidental activation of the drive stepping motor. An optional second channel in the radiation seed safe module allows the manual or automated advancement of a check cable prior to advancing the radiation seeds into and through the lumen of the sleeve.

An illustration of manual control of radiation treatment in the methods and devices of the present invention is set forth in FIGS. 7 and 8. A knob 29 for manual grasping terminates a removable plunger 26 for insertion and removal of radiation seeds 8. Detent plunger 27 and grooves 28 for distance detents locks the radiation seeds 8 at the desired position. The plunger may be removed by releasing the spring-loaded detent plunger 27. The assembled apparatus of FIG. 9 shows attachment of a housing 29, and a base and pedestal 30 suitable for a desk top procedure.

Care in preventing overstretching of the vessel graft on the sleeve 1 with balloon 4 is readily accomplished by appropriate selection of one or more balloons from a series of graduated diameter balloons of fixed size when inflated. The selected balloon or balloons can be either a single balloon or a series of balloons. An alternative arrangement is one or more spiral balloons of appropriate size that wind around the sleeve. The balloons preferably range in size from about 15 mm maximum outer diameter to about 90 mm outer diameter, in 0.5 mm increments. The surgeon measures the vessel graft diameter, selects the correct size balloon, places the balloon on the sleeve 1 and then places the vessel graft on the balloon. The balloon is inflated after complete placement within the lumen or cavity of the vessel graft. Thereafter the vessel graft is ready for irradiation. The goal of selecting the appropriate balloon is to distend the vessel graft to almost but no more than its normal diameter.

Figures 9A, 9B:
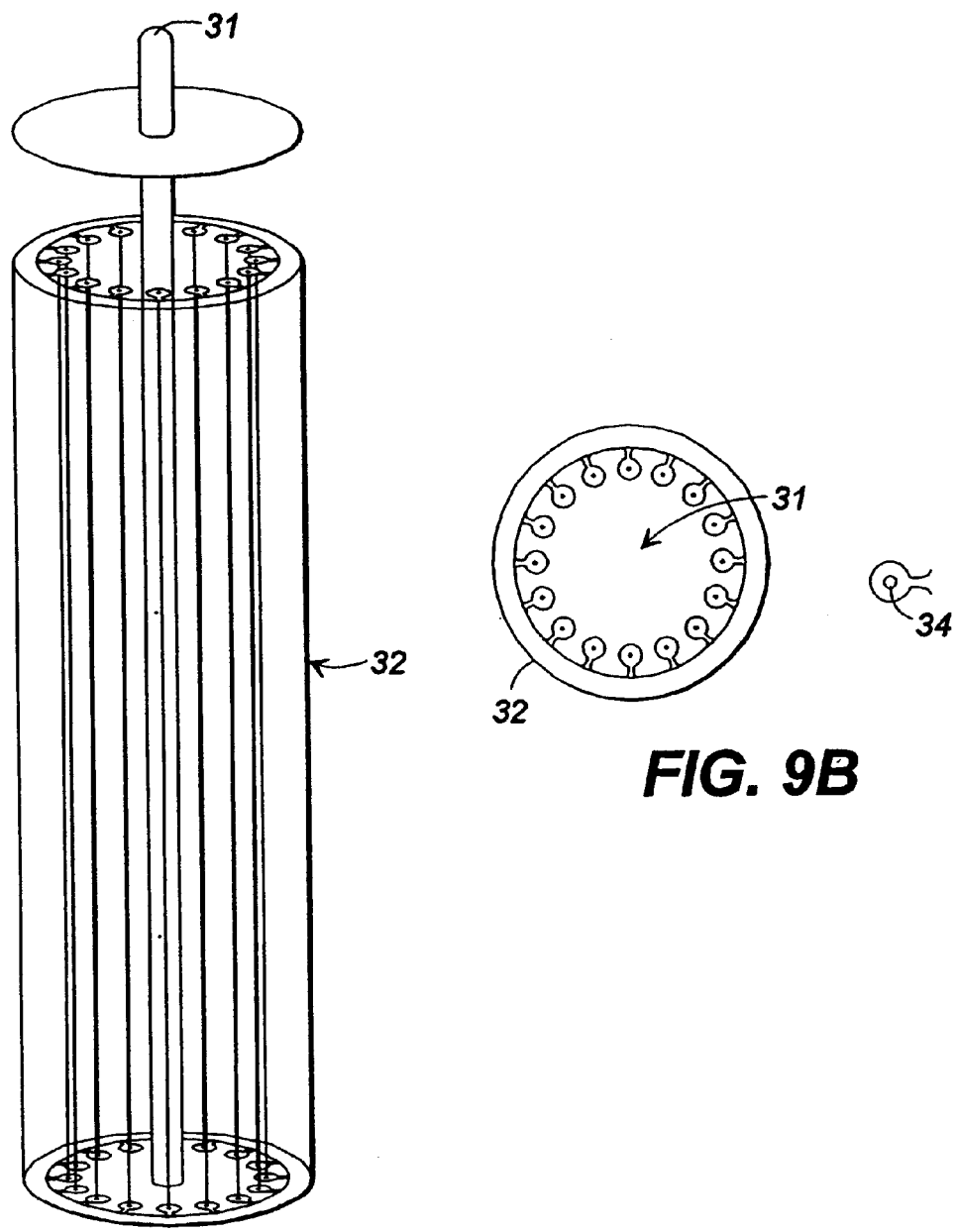
FIG. 9A schematically shows, according to one embodiment of the present invention, a cylinder with attached radiation sources for exovascular delivery of a radiation dose to a graft.
FIG. 9B schematically shows, according to one embodiment of the present invention, a cross section of the cylinder depicted in FIG. 9A, and a cross section of the attached radiation source.
Figure 10:
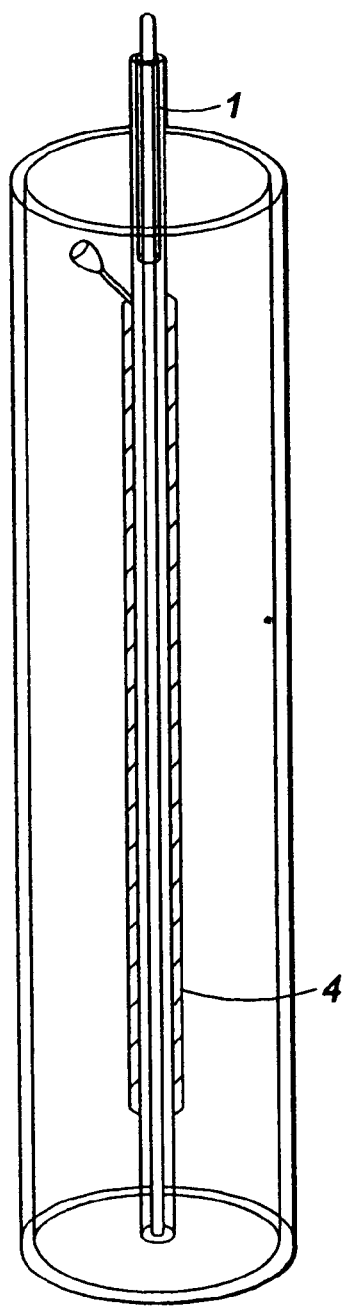
FIG. 10 schematically shows, according to one embodiment of the present invention, a cylinder of FIG. 9A with pin and balloon placed therein.

Another embodiment of the present invention covers a different class of devices that utilize radiation administered external to and outside of the vessel graft, as schematically illustrated by FIGS. 9A, 9B and 10. This apparatus is a cylinder 32, with radiation wire or linear arrays 34 of seeds placed longitudinally and in parallel to the inner central pin 31. A cross section of cylinder 32 is set forth in FIG. 9B. During irradiation treatment, the vessel graft mounted on the sleeve 1 is placed inside of the cylinder 32. In this fashion, beta or gamma irradiation can be administered from outside the vessel graft, i.e., an exovascular delivery of a radiation dose. The vessel graft (not shown) is mounted on a sleeve 1 and is then protected with a sterile thin-walled plastic cylinder (not shown) by inserting thereon the sleeve 1 with already mounted vessel graft. Once sealed in a sterile fashion within the cylinder and placed within the cylinder 32, an optional retractable shield (not shown) is removed to expose the radiation source. Administration of the dose to the vessel graft is achieved by a number of approaches, e.g., $^{90}Sr$ in the form of seeds, wire or foil, or transmuted red phosphorus ($^{32}P$) combined with malleable thermoplastic material. Several long linear sources (wires or seeds in a row) in the inner wall of the cylinder 32 are arranged so that a homogeneous dose distribution is achieved where the vessel graft is treated.

Besides the cylinder 32 with linear rows of radiation sources, other configurations for radiation delivery in the present invention readily occur to the skilled artisan. For example, a variety of chambers lined with fabricated $^{90}Sr$ foil are suitable (not shown), including containers such as a cylinder, tube, or a box. These liners may be installed in a configuration to achieve multiple treatments, e.g., a beta dose distribution to allow treatment of one to six vein segments. The vessel graft 5 mounted on a sleeve 1 is placed within the inside of the chamber, a sterile plastic liner placed therebetween to protect the mounted vessel graft from microbiological contamination of the chamber. The chamber, be it a cylinder, tube, or box may be hinged and the "clam-shell or "lid" closed to administer the dose of therapeutic irradiation. The simplest design is a $^{90}Sr$ foil-lined cylinder, sealed at one end with a thin center-post (not shown). Thin 0.5 mm sterile plastic liners can be inserted onto the sleeve and over the post. Over the post, the vessel graft on a sleeve with optional balloon is inserted and left in place for the length of time required to administer the desired dose.

In one embodiment, a strontium source is utilized to administer a therapeutic dose of beta irradiation between about 6.0 to about 18.00 Gy, preferably between about 10.0 to about 14.0 Gy. A segment of saphenous vein (usually 15 cm long but sometimes longer) is irradiated from within the lumen of the vein via an apparatus that houses and provides endovascular delivery of $^{90}$Sr radiation sources. The sources are uncovered by a retractable shield or are protruded from a housing that serves as a radiation shield.

The methods and devices of the present invention are adaptable to a variety of beta and gamma irradation sources, including, but not limited to, $^{90}$Sr, $^{90}$Y, $^{106}$Ru, $^{32}$P, $^{192}$Ir, $^{125}$I, $^{198}$Au, or $^{103}$Pd. One preferred radiation source is $^{90}$Sr. Preferred dosage ranges are between about 1.0 Gy and about 60.0 Gy, preferably between about 3.0 Gy and about 30.0 Gy, most preferably between about 6.0 Gy and about 20.0 Gy. Selecting the appropriate isotope and dosage is within the skill of the art. The desired exposure time is readily calculated for a given graft diameter, radioisotope, and sleeve geometry and size. The outward configuration of the radiation source is typically in the form of a seed, a piece of foil, a ring, a pin, or a rod.

The selected radioactive material may be contained within glass, foil, or ceramics, or, alternatively, within a powder or liquid medium, such as microparticles in liquid suspension. When solid materials are used, the preferred outer diameter of the material is approximately 0.5 mm, allowing it to be inserted into the central lumen of the vein sleeve. Such radioactive materials may be formed into pellets, spheres, and/or rods in order to be placed into the chamber of the treating element.

Various alternative treating elements may also be used to contain the radioactive material without departing from the present invention. For example, the treating elements may be toroidal, spherical, or in the form of elongated rings, and in such configurations, the radioactive material may be actually impregnated in a metal and formed into the desired shape. Alternatively, a radioactive powder may be fired to fuse the material so that it may be formed into the desired shape, which may then be encapsulated in metal, such as titanium, stainless steel or silver, or in plastic, as by dipping in molten or uncured plastic. In still another embodiment, the treating elements may be formed from a ceramic material which has been dipped in a radioactive solution In a still further alternative, the treating elements may be constructed in the form of two piece hollow cylindrical capsules having a larger-diameter half with a central cavity and a smaller-diameter half also having a central cavity, the smaller half slidably received within the larger half and bonded or welded to form the capsule structure.

The methods and devices of the present invention are suitable for any autologous coronary bypass conduit, provided that the bypass conduit is large enough. Suitable veins and arteries include, but are not limited to the long saphenous vein, the short saphenous vein, the cephalic vein, the brachiocephalic vein, or radial artery.

EXAMPLE

Ex vivo Irradiation of Saphenous Vein Graft During Coronary Artery Bypass Surgery The technique of ex vivo irradiation requires few modifications from the conventional bypass coronary artery procedure. The patient is brought into the surgery room. Monitors are attached and intravenous lines are started. The patient is put to sleep. Once the patient is asleep, the surgeon performs a median sternotomy or in some cases a lateral mini-thoractomy. The pericardium is incised and the beating heart is exposed. Canulas are positioned into the right atrium and into the aorta. The heart is stopped with cardioplege solution and the bypass perfusion pump is started to circulate blood through the body in the place of the beating heart. Incisions are made on the inner aspect of one or both legs. The saphenous vein is dissected from the fatty tissues of the medial leg. The vein is checked for leaks by distending with saline or thereafter sterile fluid under pressure. Branching venules are ligated and leaks are repaired. The vein is cut to a 15 cm length. After the vein is resected, inspected, and repaired, a radiation treatment sleeve is selected by the surgeon based upon the diameter of the saphenous vein when it was filled with blood when still in the patient's leg. After the correct sleeve is selected, it is placed into the lumen of the graft so that the vein is "impaled" upon the sleeve. Then, the sleeve mounted with saphenous vein is attached via adaptor to the base and pedestal with clear plastic hood. Then, a detachable safe (containing radiation seeds) with mechanical or automated control units is attached via adaptor to the sleeve mounted with saphenous vein. A treatment time and treatment plan are selected from an atlas or devised upon a miniature treatment planning computer for a treatment upon the size of the treatment sleeve. Then, after the clear plastic hood is lowered, radiation seeds of $^{90}$Sr are placed by remote control into the sleeve mounted with saphenous vein, and thus in effect into the lumen of the saphenous vein graft segment. A dose of 20.0 Gy is administered. The radiation seeds are then withdrawn by remote control from the lumen of the saphenous vein graft segment. The vein is removed from the sleeve and handed to the surgeon. Then, one end of the vein is sewn to an incision into the aorta and the other end is sewn to the coronary artery just beyond an angiographically detected blockage of the artery.

This procedure is repeated until all coronary arteries with significant blockages are bypassed, so that blood coming through the saphenous vein graft from the aorta to the coronary artery bypasses the blocked or occluded areas to perfuse the heart muscle. Then, the heart beat is restarted, the perfusion pump is removed, the patient's heart begins to circulate his own blood. Chest tubes are placed through the chest wall to drain any blood into the thoracic cavity to a sealed collecting system outside of the patient. The chest incision is then closed with sternal wires and with sutures. The patient is taken the cardiovascular intensive care unit and allowed to awaken.

While the foregoing specification teaches the principles of the present invention, with examples provided for the purpose of illustration, it will be understood that the practice of the invention encompasses all of the usual variations, adaptations, modifications or deletions as come within the scope of the following claims and its equivalents.

What is claimed is:

1. A method of reducing overgrowth of vascular repair tissue in coronary bypass conduit grafts, comprising:
    (a) providing a graft harvested ex vivo from a mammal;
    (b) subjecting the graft to ex vivo irradiation with a dose effective for reducing fibrointimal proliferation or neointimal hyperplasia, to give a treated graft; and
    (c) surgically implanting the treated graft into a mammal.

2. The method of claim 1, wherein the coronary bypass conduit graft is removed from the long saphenous vein, the short saphenous vein, the cephalic vein, the brachiocephalic vein, or radial artery.

3. The method of claim 1, wherein the irradiation is beta irradiation from within the lumen of the graft.

4. The method of claim 1, wherein the irradiation comes from X-rays from a micro X-ray source within the lumen of the graft.

5. The method of claim 1, wherein the irradiation comes from the gamma emitting radionuclide $^{125}I$.

6. The method according to claim 1, wherein the mammal is a human.

7. The method according to claim 1, wherein the dose is limited to a range of between about 1.0 Gy and about 60.0 Gy.

8. The method according to claim 1, wherein the dose is limited to a range of between about 3.0 Gy and about 30.0 Gy.

9. The method according to claim 1, wherein the dose is limited to a range of between about 6.0 Gy and about 20.0 Gy.

10. The method according to claim 1, wherein the radiation source is $^{90}Sr$.

11. A method of reducing fibrointimal proliferation or neointimal hyperplasia in coronary bypass vein grafts, comprising:

(a) providing a vein harvested ex vivo from a human, said vein selected from the long saphenous vein and the short saphenous vein;

(b) subjecting the vein to beta irradiation from within the lumen of the vein, with a dose effective for reducing fibrointimal proliferation or neointimal hyperplasia, the dose ranging from between about 6.0 Gy and about 20.0 Gy of $^{90}Sr$, to give a treated vein; and (c) surgically implanting the treated vein into same human.

* * * * *